United States Patent [19]

Fujio et al.

[11] Patent Number: 5,250,425
[45] Date of Patent: Oct. 5, 1993

[54] PROCESS FOR PRODUCING ASCORBIC ACID-2-PHOSPHATE

[75] Inventors: Tatsuro Fujio, Hofu; Sadao Teshiba, Machida; Akihiko Maruyama, Kawasaki; Satoshi Koizumi, Machida, all of Japan

[73] Assignee: Kyowa Hakko Kogyo Co., Ltd., Tokyo, Japan

[21] Appl. No.: 717,332

[22] Filed: Jun. 21, 1991

[30] Foreign Application Priority Data

Jun. 21, 1990 [JP] Japan .................................. 2-163877

[51] Int. Cl.$^5$ ...................... C07H 21/04; C12N 9/12; C12N 15/54; C12P 9/00
[52] U.S. Cl. ...................... 435/131; 435/132; 435/194; 435/320.1; 435/252.33; 435/874; 536/23.2
[58] Field of Search ............. 435/131, 189, 172.3, 435/320.1, 252.33, 874, 123, 132, 137, 194; 536/23.2

[56] References Cited

FOREIGN PATENT DOCUMENTS 0272064 6/1988 European Pat. Off. .
0319130 6/1989 European Pat. Off. .

OTHER PUBLICATIONS

Maruyama, A. et al., "Enzymatic Production of Ascorbic Acid-2-phosphate," Agric. Biol. Chem., 54(9), 2309-2313, (1990).

Primary Examiner—Robert A. Wax
Assistant Examiner—Dian Jacobson
Attorney, Agent, or Firm—Antonelli, Terry, Stout & Kraus

[57] ABSTRACT

Disclosed is a process for producing ascorbic acid-2-phosphate which comprises the steps of reaction, in aqueous medium, of ascorbic acid with a phosphate donor in the presence of cells, treated cells, a culture broth or a treated culture broth, of a microorganism belonging to the genus Escherichia and carrying a recombinant DNA comprising a gene isolated from a microorganism belonging to the species *Pseudomonas azotocolligans* and coding for ascorbic acid-phosphorylating enzyme until a recoverable amount of ascorbic acid-2-phosphate is accumulated in the aqueous medium, and recovery of ascorbic acid-2-phosphate therefrom.

10 Claims, 4 Drawing Sheets

—Xbal+SphI

—T4polymerase

—ligation

−XbaI+SphI

−T4polymerase

−ligation

PROCESS FOR PRODUCING ASCORBIC ACID-2-PHOSPHATE

BACKGROUND OF THE INVENTION

Ascorbic acid (hereinafter referred to as AsA) is widely used, for example, in the fields of medicines, foodstuffs and cosmetics, but has the disadvantage that it is susceptible to thermal and oxidative degradation. In order to overcome this disadvantage, various derivatives of AsA have been reported. One of the most promising derivatives among them is ascorbic acid-2-phosphate (hereinafter referred to as AsA2P), which shows remarkably high stability in vitro, and is easily converted into AsA in vivo.

Several approaches to synthesize AsA2P by chemical methods have been known (Japanese Published Examined Patent Application Nos. 30328/70, 18191/77 and 15605/73). Chemical phosphorylation of AsA, however, has the problem that various other phosphoric esters of AsA are formed besides the desired AsA2P and that complicated steps for purification of AsA2P are required to eliminate the undesired products. Thus, the chemical phosphorylation of AsA is laborious and expensive.

Compared to the chemical methods microbiological or, enzymatic phosphorylation of AsA (Japanese Published Unexamined Patent Application Nos. 214190/78, 273489/78, 199590/89 and 42996/90) is considered to be more advantageous, in that phosphorylation takes place at a specific site, in this case, at the C-2 position. However, the microorganisms so far proposed for this purpose are of low activity and conversion efficiency of AsA to AsA2P is generally in sufficient for industrial production of AsA2P. Therefore, it has been desired to develop a more efficient process for the preparation of AsA2P.

As a result of extensive studies in process for producing AsA2P, it has now been found that AsA2P can effectively be prepared from AsA and a phosphate donor, by constructing a recombinant DNA comprising a gene isolated from a microorganism belonging to the genus Pseudomonas and coding for AsA phosphorylating enzyme, transforming a microorganism belonging to the genus Escherichia with the recombinant DNA and converting AsA and a phosphate donor into AsA2P by use of the transformed microorganism as an enzyme source.

SUMMARY OF THE INVENTION

The present invention is directed to a process for producing AsA2P from AsA and a phosphate donor efficiently by the enzymatic method. The invention concerns a DNA coding for AsA-phosphorylating enzyme, isolated from a microorganism belonging to the genus Pseudomonas and its open reading frame, and a microorganism belonging to the genus Escherichia and carrying a recombinant DNA containing the DNA. Another aspect of the invention relates to a process for producing AsA-phosphorylating enzyme by culturing the transformed microorganism.

In accordance with the present invention, there is provided a process for preparation of AsA2P which comprises reacting, in an aqueous medium, AsA and a phosphate donor in the presence of cells, treated cells, a culture broth or a treated culture broth, of a microorganism belonging to the genus Escherichia and carrying a recombinant DNA having a gene coding for AsA-phosphorylating enzyme, as defined in the Sequence Listing by SEQ ID No: 1, until AsA2P is accumulated in the aqueous medium; and recovering AsA2P therefrom.

DETAILED DESCRIPTION OF THE INVENTION

The gene coding for AsA-phosphorylating enzyme from various microorganisms can be cloned for use in the present invention. Any microorganism, as far as it exhibits AsA-phosphorylating enzyme activity, can potentially serve as the nucleic acid source for the molecular cloning of the gene coding for AsA-phosphorylating enzyme. A microorganism belonging to the genus Pseudomonas and having AsA-phosphorylating enzyme activity is preferred. A preferred example is *Pseudomonas azotocolligans* ATCC 12417.

The DNA containing the gene coding for AsA-phosphorylating enzyme may be obtained by standard procedures known in the art, from a DNA library prepared by cloning chromosomal DNA or fragments thereof, as purified from the microbial cells of the genus Pseudomonas, into a suitable vector for propagation of the gene (See for example, Maniatis et al., 1982, Molecular cloning, A Laboratory Manual, Cold Spring Harbor Laboratory, Cold Spring Harbor, N.Y.; Glover, D. M. (ed.)).

A chromosomal DNA of a microorganism belonging to the genus Pseudomonas is prepared by the method described in the EMBO Journal, 4, 1875 (1985). In the molecular cloning of the gene from chromosomal DNA, fragments are generated, some of which will contain the desired gene coding for AsA-phosphorylating enzyme. The DNA may be cleaved at specific sites using various restriction enzymes, for example, BamHI, HindIII, etc. Once the DNA fragments are generated, DNA libraries are prepared using an appropriate cloning and/or expression vector. Possible vectors include, but are not limited to, plasmids or phage vectors, and the vector must be autonomously replicable in the host cell used. For *E. coli* such vectors include, but are not limited to, high copy plasmids autonomously replicable in the host cell used such as pBR322 [Gene, 2, 95 (1977)] and pUC19 [Gene, 33, 103 (1985)]. DNA libraries, a mixture of recombinant DNA molecules, can be introduced into host cells via transformation, transfection, electroporation, etc.

In our specific embodiment, *E. coli* library of *Pseudomonas azotocolligans* DNA is used for transformation of *Escherichia coli*, for example, MM294 (ATCC 33625) strain by the method of Cohen et al. [Proc. Natl. Acad. Sci. USA, 69, 2110 (1979)]. Since the plasmids such as pBR322 and pUC19 confer the resistance to a drug on the host cell, transformants in which the recombinant DNA molecule has been introduced, can be selected by using the phenotype of the resistance to a drug. Identification of specific clones harboring a recombinant DNA containing the gene coding for AsA-phosphorylating enzyme may be accomplished in a number of ways.

In a preferred embodiment, the recombinant DNA containing the gene coding for AsA-phosphorylating enzyme can be isolated from plasmid library by virtue of its homology to a radiolabelled, synthetic nucleotide probe. That is, the transformants are fixed on a nitrocellulose filter and hybridized with the synthetic oligonucleotide probe, the DNA sequence of which was deduced from a portion of amino acid sequence of purified AsA-phosphorylating enzyme from a microorganism belonging to the genus Pseudomonas [method of Grustein-Hogness, Proc. Natl. Acad. Sci. USA, 72, 3961 (1975)]. The clones which are strongly hybridized are selected as the candidate transformants carrying the recombinant DNA containing the gene coding for AsA-phosphorylating enzyme. The DNA probe is synthesized by a conventional triester method [J. Am. Chem. Soc., 97, 7372 (1975)]. The recombinant DNAs are isolated from the candidate clones and it is confirmed that the recombinant DNAs contain the gene coding for AsA-phosphorylating enzyme by the Southern method [J. Mol. Biol., 98, 503 (1975)]. After subcloning by the appropriate way, the gene coding for AsA-phosphorylating enzyme may be introduced into a microorganism belonging to a different genus. A large number of host-vector systems known in the art may be used, for example, the host-vector systems of the genus Serratia, the genus Corynebacterium, the genus Brevibacterium, the genus Pseudomonas, the genus Bacillus, etc.

In our specific embodiment, *Escherichia coli* SK14 carrying recombinant DNA pSK14, which contains AsA-phosphorylating enzyme gene cloned from *Pseudomonas azotocolligans* ATCC 12417, can be used for preparation of AsA2P from AsA and a phosphate donor. *Escherichia coli* SK14 has been deposited on Jun. 15, 1990 under the Budapest Treaty in the Fermentation Research Institute, the Agency of Industrial Science and Technology of Japan under access number FERM BP-2970.

The microorganism having the enhanced AsA-phosphorylating activity can be grown in a conventional manner known in the art. That is, the microorganism can be grown in a conventional medium containing carbon sources, nitrogen sources, inorganic materials, amino acids, vitamins, etc. under aerobic conditions, while the temperature, the pH, etc. are kept constant.

As the carbon sources, various carbohydrates such as glucose, fructose, sucrose, molasses, blackstrap molasses, hydrolyzates of starch, etc.; alcohols such as ethanol, glycerin, sorbitol, etc.; organic acids such as pyruvic acid, lactic acid, acetic acid, etc.; amino acids such as glycine, alanine, glutamic acid, aspartic acid, etc. are used. Any of the carbon sources may be used so long as the microorganisms can assimilate them. A concentration of the carbon sources is preferably 5 to 30%.

As the nitrogen sources, ammonia, various inorganic or organic ammonium salts such as ammonium chloride, ammonium sulfate, ammonium nitrate, ammonium carbonate, ammonium acetate, ammonium phosphate, etc.; amines; other nitrogen-containing compounds such as urea, NZ amine, meat extract, yeast extract, cornsteep liquor, casein hydrolyzates, fish meal or its digested product, etc. are used. A concentration of the nitrogen sources is generally 0.1 to 10%.

As the inorganic material, potassium dihydrogen phosphate, dipotassium hydrogen phosphate, magnesium phosphate, magnesium sulfate, sodium chloride, ferrous sulfate, zinc sulfate, calcium carbonate etc. are used. If necessary and desired, amino acids, nucleic acids, vitamins, etc. required for growth of the microorganism may be supplemented to the medium.

The microorganism is cultured under aerobic conditions with shaking flasks or supplying oxygen by aeration and/or agitation in a mechanical fermentor. Temperature of the culture is preferably 20° to 40° C. The pH of the medium during the culture is maintained around neutral with ammonia, urea, sodium hydroxide solution, etc. The microorganism is grown preferably for 10 to 48 hours.

The AsA-phosphorylating enzyme can be isolated and purified from cultured cells of the microorganisms in an ordinary technique. The enzyme, for example, can be purified as follows. The cells harvested by centrifugation are disrupted by ultrasonic oscillation. The cell extracts thus obtained are purified in an ordinary skill such as fractionation with ammonium sulfate, step-wise chromatography such as ion-exchange, chromatofocusing, gel filtration, etc.

The enzyme reaction for producing AsA2P from AsA and a phosphate donor is carried out by reacting in an aqueous solution under an acidic condition, ascorbic acid with a phosphate culture broth of the suitable microorganism. Usually, AsA2P is formed by mixing cells, treated cells, culture broth or treated culture broth, of the suitable microorganism with AsA and a phosphate donor in an aqueous solution.

The efficiency in forming AsA2P can be improved by adding a surfactant, an organic solvent, etc., depending upon necessity.

Any surfactant may be used so long as it can accelerate the reaction for producing AsA2P from AsA and a phosphate donor. The surfactants include, but are not limited to, cationic surfactants such as polyoxyethylene stearylamine (e.g., Nymeen S-215, manufactured by Nippon Oil and Fats Co., Ltd.), cetyltrimethyl ammonium bromide, etc.; anionic surfactants such as sodium oleylamide sulfate, etc.; nonionic surfactants such as polyoxyethylene sorbitan monostearate (e.g., Nonion ST221, manufactured by Nippon Oil and Fats Co. Ltd.), etc. These surfactants may be used in a concentration of generally 1 to 50 mg/ml, preferably 1 to 20 mg/ml.

As the organic solvent, there may be used toluene, xylene, acetone, aliphatic alcohols, benzene, ethyl acetate, etc., in a concentration of 0.1 to 50 ml/l, preferably 1 to 20 ml/l.

AsA and a phosphate donor may be used either in the form of a chemically purified product or in the form of a crude product, so long as the product does not prevent the formation of AsA2P. In an aqueous medium, AsA and the phosphate donor may be used in a concentration range of 1 to 1000 mM and 1 to 1000 mM, respectively.

As the phosphate donor, there may be used adenosine triphosphate (ATP), p-nitrophenyl phosphate, acetyl phosphate, pyrophosphoric acid, triphosphoric acid, tetrapolyphosphoric acid, polyphosphoric acid and the like.

The enzyme reaction is carried out at a temperature of 20° to 70° C. for 0.5° to 48° hours, while keeping the pH in an acidic range, preferably at 3 to 4.2.

The treated culture broth is exemplified by a concentrate of the culture broth, dried culture broth, surfactant-and/or organic solvent-treated culture broth and acetone-treated culture broth. The treated cells is exemplified by dried cells, acetone-treated cells, surfactant-and/or organic solvent-treated cells, lytic enzyme-treated cells, immobilized cells and cell extracts, etc.

Where the cells are used for preparation of AsA2P as the enzyme source, the cells are used in a range of 1 to 400 mg per ml of an aqueous medium, based on the wet cell weight.

AsA2P can be quantitatively determined by measuring absorption at 254 nm by high performance liquid chromatography using Particle 10 SAX column [manufactured by Whatman Co., Ltd.], using as a standard, the pure product prepared by chemical synthesis.

After the cells and proteins are removed from the reaction mixture by centrifugation, a supernatant is neutralized. AsA2P is obtained from the supernatant by step-wise chromatography such as ion exchange resin, Sephadex and high performance liquid chromatography.

The present invention is described in detail with reference to the following examples. Reagents and vectors used for genetic engineering works were all purchased from Takara Shuzo Co. Ltd., and other reagents were purchased from Nakarai Tesque Co. Ltd.

EXAMPLE 1

Purification of AsA-phosphorylating enzyme

Pseudomonas azotocolligans ATCC 12417 strain was cultured in KM102 medium (pH 7.2) containing 10 g polypeptone, 7 g meat extract, 5 g yeast extract and 3 g NaCl in one liter of deionized water, and 570 g (based on wet cell weight) of the resulting cultured cells was disrupted with Manton-Gaulin homogenizer (manufactured by Manton-Gaulin Mfg.) to prepare cell extracts. After nucleic acid was removed with protamine sulfate precipitation, the extracts were fractionated by salting out with solid ammonium sulfate to 30 to 50% saturation. The precipitates formed were collected by centrifugation and dissolved in one liter of 0.01M potassium phosphate buffer (pH 7.0). The resulting solution was passed through a CM-Sepharose column (7.4×19 cm), previously equilibrated with 0.02M potassium phosphate buffer (pH 6.0). After washing the column with the buffer, the enzyme was eluted with a linear gradient of 0 to 0.25M NaCl in the buffer. Active fractions were combined and concentrated with YM10 membrane (manufactured by Amicon Co. Ltd.). After the buffer was exchanged with 25 mM triethylamine hydrochloride (pH 11.0), the concentrate was passed through PBE118 column (1.4×55 cm, manufactured by Pharmacia Fine Chemicals, Inc.) previously equilibrated with the same buffer. Enzyme was eluted with Pharmalyte pH8-10.5-HCl (pH 7.5). The active fractions were combined and concentrated by using YM10 as described before. The concentrate was passed through a Sephadex G-75 column (2.3×80 cm, manufactured by Pharmacia Fine Chemicals, Inc.), previously equilibrated with 0.02M potassium phosphate buffer (pH 7.0). The protein was eluted with the same buffer, and concentrated by the same method as described before, and finally 5 mg of the purified AsA-phosphorylating enzyme was obtained.

Physico-chemical properties of the enzyme thus obtained are shown below.
(1) Molecular weight: 29,000 when determined by SDS-PAGE; 31,500 when determined by gel filtration.
(2) Km value;
   for ascorbic acid: 100 mM or more
   for ATP: 40 mM
   for pyrophosphoric acid: 10 mM
(3) Optimum pH;
   About 5.5 when ATP was used as a phosphate donor;
   about 4.4 when pyrophosphoric acid was used as a phosphate donor.
(4) Optimum temperature; About 55° C.
(5) Thermostability; The activity is lost by about 33% by heat treatment at 60° C. for 30 minutes.
(6) Inhibition; The activity of the enzyme is inhibited by $Cu^{2+}$.

EXAMPLE 2

Isolation of DNA

Pseudomonas azotocolligans ATCC12417 cells were inoculated into an L liquid medium (pH 7.2) containing 10 g Bactotrypton, 5 g yeast extract, 5 g sodium chloride in one liter of deionized water, and grown at 37° C. overnight. After 0.6 g of the cultured cells were suspended in 10 ml of 0.1M NaCl (pH 8.5) containing 0.1M disodium ethylenediamine tetraacetate (EDTA), 1.1 ml of 1M Tris-hydrochloride buffer (pH 9.0) containing 10% sodium laurylsulfate and 5 mg of proteinase K was added to the suspension. The mixture was allowed to stand at 42° C. for one hour. After addition of 12 ml of phenol saturated with 10 mM Tris-hydrochloride buffer (pH 8.0) containing 1 mM EDTA, the mixture was thoroughly stirred. The solution was centrifuged and 12 ml of the aqueous layer was collected. After 1.2 ml of 2.5M sodium acetate was added to the aqueous layer, 30 ml of ethanol was further added thereto. The precipitated chromosomal DNA was wound up around a glass rod and dried. Then, the chromosomal DNA was dissolved in 3 ml of 10 mM Tris-hydrochloride buffer containing 1 mM EDTA, and ribonuclease was added to the solution in a concentration of 50 μg/ml. The resulting mixture was allowed to stand at 37° C. for 30 minutes. An equal volume of chloroform was added to the solution, and the mixture was thoroughly stirred, and centrifuged. After 3 ml of the aqueous layer was collected 0.3 ml of 2.5M sodium acetate was added to the aqueous layer and 30 ml of ethanol was further added thereto. The precipitated chromosomal DNA was wound up around a glass rod and dried to a purified chromosomal DNA. Then, the purified chromosomal DNA was suspended in 1 ml of 10 mM Tris-hydrochloride buffer (pH 8.0) containing 1 mM EDTA.

EXAMPLE 3

Preparation of recombinant DNA

By adding 10 units of BamHI to the suspension containing 1 μg of the chromosomal DNA obtained above, digestion was performed. Separately 5 units of BamHI was added to 20 μl of solution containing 1 μg of vector pUC19 to conduct full digestion. Then 2 μl of 1M Tris-hydrochloride buffer (pH 8.0) was added to the digestion mixture and 5 units of alkaline phosphatase was further added thereto. The reaction was carried out at 65° C. for an hour. Each of the resulting chromosomal DNA and vector DNA was isolated by the phenol extraction and ethanol precipitation described above. After 100 ng of the purified chromosomal DNA and 20 ng of the purified vector DNA were suspended in T4 ligase buffer [66 mM Tris-hydrochloride buffer (pH 7.6), 6.6 mM magnesium chloride, 10 mM dithiothreitol and 0.1 mM ATP], 10 units of T4 ligase was added to the suspension. The reaction was carried out at 16° C. for 16 hours to ligate both DNAs, whereby a mixture of various recombinant DNA molecules was obtained.

EXAMPLE 4

Selection of the recombinant DNA containing a gene coding for AsA-phosphorylating enzyme The mixture of various recombinant DNA molecules obtained in Example 3 was used for transformation of *Escherichia coli* MM294 strain (ATCC 32625) according to the method of Cohen et al. [Proc. Natl. Acad. Sci. USA, 69, 2110 (1979)]. The resulting transformants were spread on an L agar medium (L liquid medium supplemented with 1.5% agar) containing 100 mg/l ampicillin.

About 6,000 colonies resistant to ampicillin were fixed on a nitrocellulose filter. Then the colonies were tested as to hybridize with a synthetic oligonucleotide probe, the DNA sequence of which was deduced from a portion of amino acid sequence of AsA-phosphorylating enzyme. The partial amino acid sequence was determined as follows. Purified AsA-phosphorylating enzyme obtained in Example 1 was reduced, carboxyamidomethylated with iodoacetamide, and treated with TPCK-trypsin in 100 mM ammonium hydrogencarbonate (pH 8.0) at 37° C. for 24 hours. The product was fractionated by high performance liquid chromatography (HPLC) to give trypsin-treated peptide TR9 and TR19 of AsA-phosphorylating enzyme. Amino acid sequence of TR9 and TR19 were determined by the method well known in the art.

Among the about 6,000 colonies, two strains were strongly hybridized at 45° C. with a $^{32}$P-labelled oligonucleotide probe, the DNA sequence of which was deduced from the amino acid sequence of peptide TR19 and defined in the Sequence Listing by SEQ ID No. 3 and illustrated below:

```
5'                          3'
GC AAT GGG AAT GGT ACT
    G    G     GT    17 mer
    C    C     C
    T    T     T
```

(where in the third nucleotide is any one of A, G, C, and T; the ninth nucleotide is any one of A, G, C and T; the fifteenth nucleotide is any one of A, G, C and T; and the sixteenth nucleotide is C or T; which make 128 synthetic DNA mixtures). Hybridization was done according to the method of Gruntstein-Hogness [Proc. Natl. Acad. Sci. USA., 72, 3961 (1975)]. With respect to the two strains obtained, it was found according to the method of Southern [J. Mol. Biol., 98, 503 (1975)], that the strains were strongly hybridized both with the aforesaid probe and with synthetic DNA probe corresponding to the amino acid sequence of another trypsin-treated peptide TR9, defined in the Sequence Listing by SEQ ID No. 4 and illustrated below:

```
5'                       3'
T CAC AAA T AGG ACC ATC
  G   G    G   G   G
      T    C   C
      T        T
```

Figure 1:
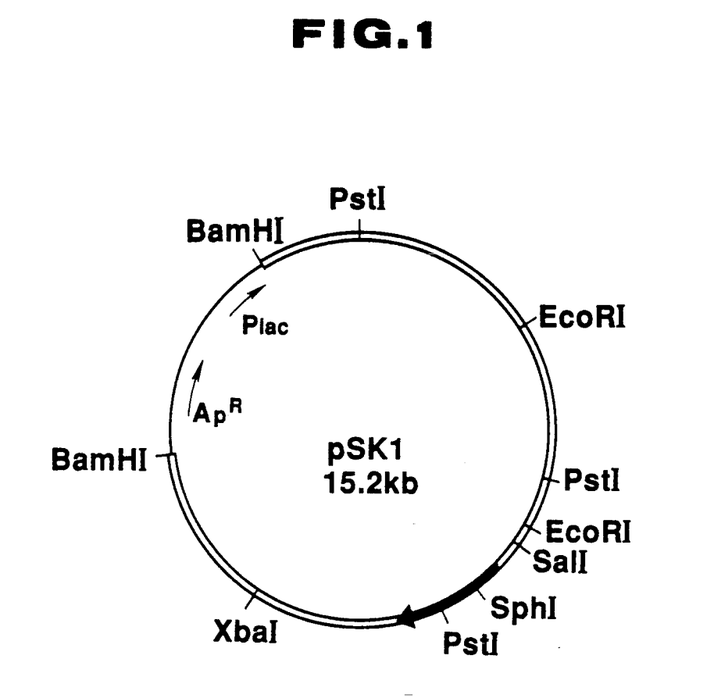
FIG. 1 shows restriction enzyme map of plasmid pSK1.
Figure 2:
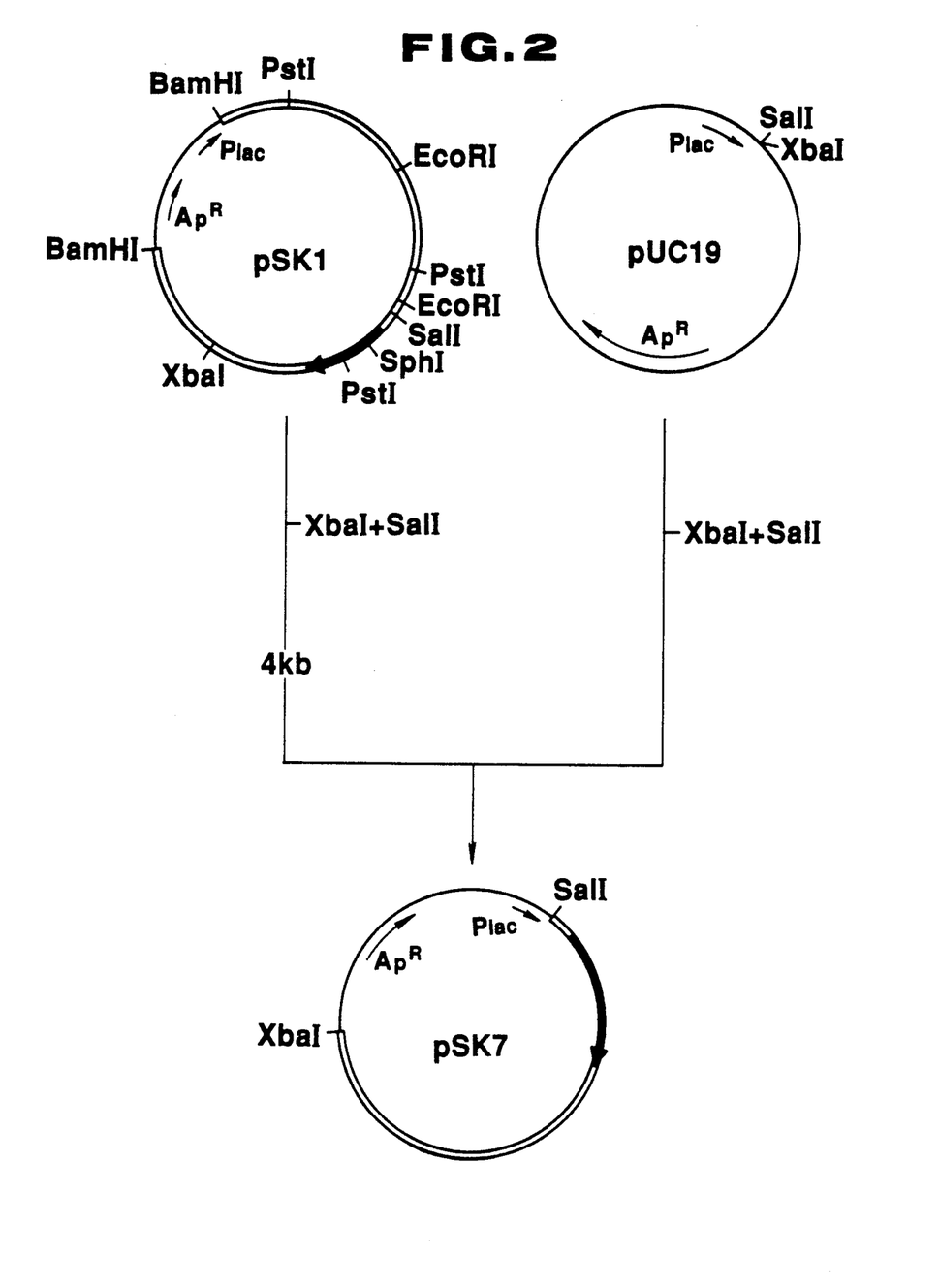
FIGS. 2, 3 and 4 show steps of constructing plasmids pSK7, pSK8 and pSK14, respectively.
Figure 3:
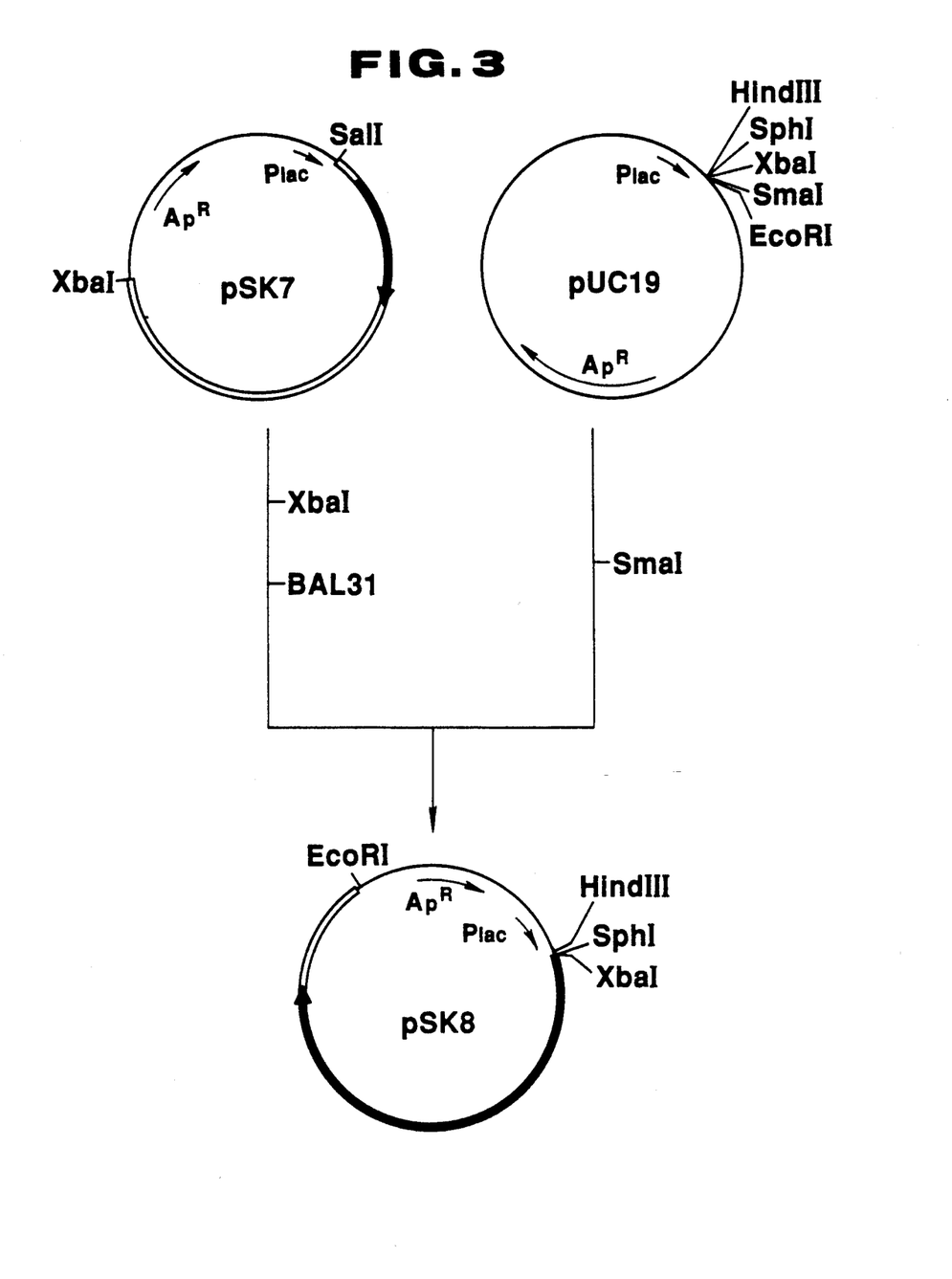
Figure 4:
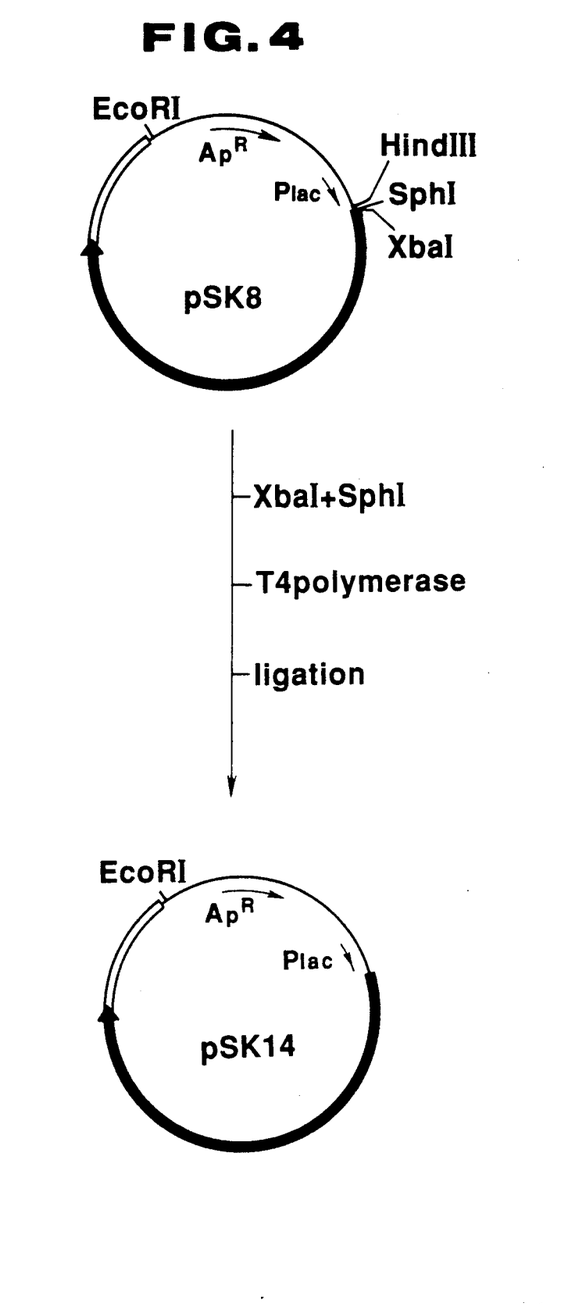

(where in the third nucleotide is A or G; the sixth nucleotide is any one of A, G, and T; the ninth nucleotide is any one of A, G, C and T; the twelfth nucleotide is any one of A, G, C and T; and the fifteenth nucleotide is A or G; which make 192 synthetic DNA mixtures). The plasmids carried by the two strains had the same structure, and were found to have a 12.5 kb chromosomal DNA fragment derived from *Pseudomonas azotocolligans* ATCC 12417 at the BamHI site of pUC19. The plasmids were named pSK1. A restriction enzyme map of pSK1 is shown in FIG. 1.

EXAMPLE 5

Subcloning of the gene:

It is presumed that the gene coding for AsA-phosphorylating enzyme is present on the SalI-XbaI region in the inserted fragment of pSK1 plasmid.

Twenty units of XbaI and 60 units of SalI were added to 50 μl of a solution containing 2 μg of plasmid pSK1 DNA obtained above to conduct complete digestion. Then, a 4 kb fragment containing the structural gene was isolated and purified by agarose gel electrophoresis [Maniatis et al., Molecular Cloning, Cold Spring Harbor Laboratory (1982)]. Separately, 10 units of XbaI and 30 units of SalI were added to 20 μl of a solution containing 1 μg of vector pUC19 for complete digestion. Then a vector DNA fragment was isolated by consecutive phenol extraction and ethanol precipitation described above. Using 10 units of T4 DNA ligase, 100 ng of the 4 kb DNA fragment isolated from the purified pSK1 was ligated with 50 ng of the purified vector DNA at 16° C. for 16 hours in T4 ligase buffer. *Escherichia coli* MM294 strain was transformed with the thus obtained recombinant DNA to select ampicillin-resistant transformants.

The plasmid DNA was isolated and purified from these transformants and its structure was analyzed. The plasmid DNA was observed to have the structure in which DNA fragment containing the gene coding for AsA-phosphorylating enzyme isolated from pSK1 has been inserted into pUC19 downstream lac promoter of pUC19. The plasmid DNA was named pSK7.

EXAMPLE 6

Determination of nucleotide sequence of the gene coding for AsA-phosphorylating enzyme on plasmid pSK7

Nucleotide sequence of the thus obtained gene coding for AsA-phosphorylating enzyme which was inserted into plasmid pSK7 was determined according to the dideoxy method [Messing, J., Methods in Enzymol., 101, 20 (1983)]. The structural gene of the AsA-phosphorylating enzyme has the nucleotide sequence as defined in the Sequence Listing by SEQ ID No: 1 and illustrated in:

TABLE 1

| | | | |
|---|---|---|---|
| ATGATCCGCG | GTGGCATCTT | CGCAGCGCTC | TCGCTGCTCA |
| TCGCGGTCCC | TCAGGCGAGT | GACACGGCGC | CGTACCTCGC |
| CGCGGGCCAA | TATCCCGACG | GCATGGCGAT | CCTGCCGCCG |
| CCGCCGGCGC | TCGACAGCCC | CGGCGCTGCC | CTGGACATGG |
| CGGTGTTCCG | GGCAACGCGG | AAGCTGGAGG | GCACCCCGCG |

TABLE 1-continued

| | | | |
|---|---|---|---|
| CTGGCGGATC | GCCACCGACG | ACGTCACCAA | CGATCCGCTG |
| CGCCGCAACG | CCTGCGCGAT | GGGGATGGTG | CTCGACGTCA |
| AGACTGCGCC | GGCACTTGCC | CGGCTGCTCG | ATCGCGCAGG |
| CACGGGCCCG | GTCGTCGGCA | GGGTGAAGGC | TGCCTACCAA |
| GTGCCGCGTC | CCTATCTGCG | CGAGGACGGC | CCGATCTGCG |
| AGGCCAAGAC | CGCACATCTC | GCCAGCAATG | GCGACTACCC |
| GTCGGGGCAC | ACCGCCAATG | GTTGGCTGGA | AGCGCAGATC |
| CTCGCCGAGG | TGATGCCCGA | CAAGGCGACT | GCGATCCTCG |
| CGCGCGGCCG | TGCCTATGGC | GAGAGCCGGG | CGATTTGCGG |
| GTCGCACAGC | AAGAGCGCGG | TCGAAGCCGG | CTACATGGCC |
| GGCGCCTCGG | TGTTCGCGGT | GCTGCAGACC | TCGCCCGCCT |
| ACCAGCGGGA | TCTCGCGGCG | GCGCGGCAGG | AAGCGGCGCG |
| GCTGCGCACT | ACCGCGCCGC | GCCCCGATGC | ACAAAGCTGT |
| GTCGCGGAAG | CGGAGGCCCT | TCGCGTCCGC | CCCTGG |

EXAMPLE 7

Preparation of AsA2P

With the recombinant DNA pSK7 obtained in Example 5, Escherichia coli MM294 was transformed. The resulting ampicillin-resistant cell was inoculated into 10 ml of LAp medium (L liquid medium supplemented with 100 mg/l ampicillin), and cultured at 30° C. for 24 hours. The resulting culture, 0.4 ml, was inoculated into 40 ml of LAp medium, and cultured at 36° C. for 16 hours. The culture was centrifuged at 8000 rpm for 10 minutes to collect cells. The cells were frozen and stored at −20° C. With stirring 50 ml of a reaction mixture containing 50 mg/ml of the frozen and stored cells, 0.4M ascorbic acid, 0.2M pyrophosphoric acid and 4 g/l Nymeen S-215 at 900 rpm with a magnetic stirrer, the reaction was carried out at a pH 4.2, 40° C. for an hour. In this case, the yield of AsA2P was 8.9 g/l.

EXAMPLE 8

Elimination of flanking region in the inserted fragment

It was considered that some other nucleotide sequence than the gene coding for AsA-phosphorylating enzyme (flanking region) was present upstream and downstream of the structural gene of the inserted fragment in pSK7. Therefore, plasmid pSK8 in which the flanking region had been deleted, was constructed by the following procedures.

To 120 μl of a solution containing 8 μg of pSK7 DNA was added 80 units of XbaI, and the complete digestion was performed. Further, digestion was performed with 2 units of BAL31 nuclease at 30° C. in BAL31 buffer [20 mM Tris-hydrochloride buffer (pH 8.0), 600 mM NaCl, 12 mM MgCl₂, 12 mM CaCl₂]. After the reaction was started, a portion of the reaction mixture was sampled intermittently from 40 to 60 minutes. With respect to each of reaction solutions sampled, the extraction with phenol: chloroform and the ethanol precipitation were performed to obtain a DNA fragment of 1 to 2 kb in size. Separately, 10 units of SmaI was added to 20 μl of a solution containing 1 μg of vector pUC19. Then, 2 μl of 1M Tris-hydrochloride buffer (pH 8.0) was added thereto followed by dephosphorylation at 65° C. for 40 minutes with 5 units of alkaline phosphatase. After completion of the reaction, a vector DNA fragment was obtained via the extraction with phenol: chloroform and the ethanol precipitation.

To 40 μl of T4 ligase buffer containing 100 ng of the thus obtained DNA fragment isolated from pSK7 and 50 ng of the DNA fragment isolated from pUC19 were added 10 units of T4 ligase to perform ligation at 16° C. for 16 hours. With the resulting recombinant DNA, Escherichia coli MM294 was transformed, and ampicillin-resistant transformants were selected.

The resulting transformants were cultured in a manner similar to Example 7. AsA-phosphorylating enzyme activity of the transformants was determined according to the method described in Example 11. A strain having a higher activity than that of Escherichia coli MM294/pSK7 was selected. As the result, AsA-phosphorylating enzyme activity of MM294/pSK8 strain is about 10 times as much as that of MM294/pSK7 strain. pSK8 plasmid DNA was isolated and purified, and its structure was analyzed. The inserted fragment of pSK8 plasmid DNA was deleted to about 1 kb.

EXAMPLE 9

Construction of plasmid pSK14

It was assumed that there was little flanking region left in the inserted fragment of pSK8. Further improvement was attempted using multilinker cite of pUC19 to thereby construct plasmid pSK14.

To 40 μl of a solution containing 1 μg of pSK8 DNA were added 10 units of XbaI and 10 units of SphI to complete digestion. Thereafter a fragment of about 3.7 kb was isolated and purified by agarose gel electrophoresis. The resulting DNA was changed to make blunt end in 50 μl of T4 DNA polymerase buffer [67 mM Tris-hydrochloride buffer (pH 8.8), 6.7 mM MgCl₂, 16.6 mM(NH₄)₂SO₄, 10 mM 2-mercaptoethanol, 6.7 mM EDTA, 0.33 mM dCTP, 0.33 mM dATP, 0.33 mM dGTP, 0.33 mM dTTP] using 5 units of T4 DNA polymerase.

The resulting DNA was extracted with phenol: chloroform and then precipitated with ethanol. The thus precipitated DNA was subjected to ligation reaction in 40 μl of T4 DNA ligase buffer using 5 units of T4 DNA ligase at 16° C. for 16 hours.

With the thus obtained recombinant DNA, Escherichia coli MM294 strain was transformed to obtain an ampicillin-resistant transformants.

From the transformation, plasmid DNA was isolated and purified. By its structural analysis, the plasmid was shown to have the desired structure and the plasmid was named pSK14.

EXAMPLE 10

Production of ascorbic acid phosphorylating of enzyme

With the recombinant plasmid pSK14 obtained in Example 9, Escherichia coli MM294 strain was transformed. The resulting ampicillin-resistant cell was cultured in a manner similar to Example 7. The cells were collected by centrifugation. The resulting cells were suspended in Laemmli's sample buffer [Laemmli, Nature, 227, 68 (1970)] with heating followed by SDS-polyacrylamide gel electrophoresis [the method of Laemmli, ibid.]. After Western blotting [Towbin et al., Proc. Natl. Acad. Sci, USA, 76, 4350 (1979)], enzyme antibody staining [Kazufumi Tabe, Cell Engineering, 2, 1061 (1983)] was performed using horseradish peroxidase-labelled secondary antibody [manufactured by DAKO Co., Ltd.], whereby a polypeptide band was detected at the site showing a molecular weight of about 29,000. This band was not detected in the case of using an *Escherichia coli* strain carrying vector pUC19 alone. The result reveals that the *Escherichia coli* strain bearing recombinant plasmid pSK14 produced large quantities of AsA-phosphorylating enzyme.

EXAMPLE 11

Comparison of AsA-phosphorylating enzyme activity in various plasmid-carrying strains Using the strains carrying the recombinant DNAs containing the gene coding for AsA-phosphorylating enzyme obtained in the above Examples, AsA-phosphorylating enzyme activity were examined.

Each of the recombinant DNA-carrying strains shown in the following Table 2 was cultured in a manner similar to Example 7 and the resulting cells were frozen and stored at −20° C. With stirring 2 ml of a reaction solution containing 50 mg/ml (wet cell weight) of the frozen and stored cells, 0.4M AsA, 0.2M pyrophosphoric acid and 4 g/l Nymeen S-215 at 900 rpm with a magnetic stirrer, the reaction was carried out at a pH of 4.2, 40° C. for an hour. Separately, *Pseudomonas azotocolligans* ATCC 12417 strain was cultured in a manner similar to Example 1 and the resulting cells were frozen and stored at −20° C. Using 50 g/l (wet cell weight) of the frozen and stored cells, the reaction was carried out as described above. The quantity of AsA2P produced in each reaction solution was determined by high performance liquid chromatography. A relative activity of the AsA-phosphorylating enzyme was determined based on the quantity of AsA2P produced per 1 g of the cells carrying each of the recombinant DNAs, of pSK1, pSK7, pSK8 and pSK14 (wherein the quantity of AsA2P produced per 1 g of the cells of *Pseudomonas azotocolligans* ATCC12417 is taken as 1). The results are shown in Table 2.

TABLE 2

| Strain | Cell (g/l) | AsA2P (g/l) | Relative Activity |
|---|---|---|---|
| ATCC 12417 | 50 | 4.04 | 1 |
| MM294/pSK1 | 50 | 0.10 | 0.02 |
| MM294/pSK7 | 50 | 8.90 | 2.20 |
| MM294/pSK8 | 5 | 9.25 | 22.90 |
| MM294/pSK14 | 5 | 23.54 | 58.27 |

EXAMPLE 12

Production of AsA2P

*Escherichia coli* SK14 strain was cultured in a manner similar to Example 7. The cells were frozen and and stored cells, 0.4M AsA, 0.2M pyrophosphoric acid and 4 g/l Nymeen S-215 at 900 rpm with a magnetic stirrer, the reaction was carried out at a pH of 4.2, 40° C. for 2 hours. As the result, AsA2P was produced and accumulated in the reaction solution in an amount of 34.9 g/l.

EXAMPLE 13

*Escherichia coli* SK14 strain was cultured in a manner similar to Example 7. To the culture medium obtained, 0.4M AsA, 0.2M pyrophosphoric acid and 4 g/l Nymeen S-215 were added. After adjusting pH to 4.2 with sulfuric acid, the reaction was carried out for 30 minutes with stirring at 100 rpm at 40° C. As the result, AsA2P was produced and accumulated in the reaction solution in an amount of 17.1 g/l.

What is claimed is:

1. A process for producing ascorbic acid-2-phosphate which comprises the steps of:
   i) reacting ascorbic acid with a phosphate donor in the presence of cells, treated cells, a culture broth or a treated culture broth, of a microorganism belonging to the species *Escherichia coli* which carries a recombinant DNA comprising an isolated DNA fragment containing a DNA having a nucleotide sequence defined in the Sequence Listing by SEQ ID NO: 1, in an aqueous solution under an acidic condition at a temperature of 20° to 70° C. for 0.5 to 48 hours; and
   ii) recovering ascorbic acid-2-phosphate therefrom; said treated cells being selected from the group consisting of dried cells, acetone-treated cells, cells treated with at least one of a surfactant or an organic solvent, bacteriolytic enzyme-treated cells, immobilized cells, or enzyme preparations extracted from cells; and said treated culture broth being selected from the group consisting of a concentrate of the culture broth, a dried culture broth, a culture broth treated with at least one of a surfactant or an organic solvent, and an acetone-treated culture broth.

2. An isolated DNA fragment consisting essentially of the nucleotide sequence as defined in the Sequence Listing by SEQ ID NO: 1.

3. The isolated DNA fragment according to claim 2, wherein the isolated DNA fragment is isolated from *Pseudomonas azotocolligans* ATCC 12417.

4. A recombinant DNA consisting essentially of the isolated DNA fragment according to claim 2 and a vector DNA.

5. The recombinant DNA according to claim 4, which is named pSK14 carried by *Escherichia coli* FERM BP-2970.

6. The process according to claim 1, wherein the phosphate donor is selected from the group consisting of adenosine triphosphate (ATP), p-nitrophenyl phosphate, acetyl phosphate, pyrophosphoric acid, tripolyphosphoric acid, tetrapolyphosphoric acid and polyphosphoric acid.

7. The process according to claim 1, wherein the DNA fragment is isolated from *Pseudomonas azotocolligans* ATCC 12417.

8. The process according to claim 1, wherein the microorganism belonging to the genus Escherichia is *Escherichia coli* FERM BP-2970.

9. A biologically pure culture of *Escherichia coli* FERM BP-2970.

10. A process for producing ascorbic acid-phosphorylating enzyme which comprises culturing *Escherichia coli* FERM BP-2970 in a medium to obtain a culture broth, collecting microbial cells from the culture broth and recovering ascorbic acid-phosphorylating enzyme accumulated within the cells.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 756 base pairs
      ( B ) TYPE: nucleic acid
      ( C ) STRANDEDNESS: single
      ( D ) TOPOLOGY: linear    ( i i ) MOLECULE TYPE: DNA (genomic)

( i i i ) HYPOTHETICAL: NO

( i v ) ANTI-SENSE: NO

( v i ) ORIGINAL SOURCE:
      ( B ) STRAIN: Pseudomonas azotocolligans ATCC 12417
      ( G ) CELL TYPE: Unicellular Organism    ( v i i ) IMMEDIATE SOURCE:
      ( B ) CLONE: pSK57

( i x ) FEATURE:
      ( A ) NAME/KEY: CDS
      ( B ) LOCATION: 1..756

( x i ) SEQUENCE DESCRIPTION: SEQ ID NO:1:

```
ATG ATC CGC GGT GGC ATC TTC GCA GCG CTC TCG CTG CTC ATC GCG GTC                48
Met Ile Arg Gly Gly Ile Phe Ala Ala Leu Ser Leu Leu Ile Ala Val
 1               5                  10                  15

CCT CAG GCG AGT GAC ACG GCG CCG TAC CTC GCC GCG GGC CAA TAT CCC                96
Pro Gln Ala Ser Asp Thr Ala Pro Tyr Leu Ala Ala Gly Gln Tyr Pro
                20                  25                  30

GAC GGC ATG GCG ATC CTG CCG CCG CCG GCG CTC GAC AGC CCC GGC                   144
Asp Gly Met Ala Ile Leu Pro Pro Pro Ala Leu Asp Ser Pro Gly
             35                  40                  45

GCT GCC CTG GAC ATG GCG GTG TTC CGG GCA ACG CGG AAG CTG GAG GGC              192
Ala Ala Leu Asp Met Ala Val Phe Arg Ala Thr Arg Lys Leu Glu Gly
         50                  55                  60

ACC CCG CGC TGG CGG ATC GCC ACC GAC GAC GTC ACC AAC GAT CCG CTG              240
Thr Pro Arg Trp Arg Ile Ala Thr Asp Asp Val Thr Asn Asp Pro Leu
 65                  70                  75                  80

CGC CGC AAC GCC TGC GCG ATG GGG ATG GTG CTC GAC GTC AAG ACT GCG              288
Arg Arg Asn Ala Cys Ala Met Gly Met Val Leu Asp Val Lys Thr Ala
                 85                  90                  95

CCG GCA CTT GCC CGG CTG CTC GAT CGC GCA GGC ACG GGC CCG GTC GTC              336
Pro Ala Leu Ala Arg Leu Leu Asp Arg Ala Gly Thr Gly Pro Val Val
             100                 105                 110

GGC AGG GTG AAG GCT GCC TAC CAA GTG CCG CGT CCC TAT CTG CGC GAG              384
Gly Arg Val Lys Ala Ala Tyr Gln Val Pro Arg Pro Tyr Leu Arg Glu
         115                 120                 125

GAC GGC CCG ATC TGC GAG GCC AAG ACC GCA CAT CTC GCC AGC AAT GGC              432
Asp Gly Pro Ile Cys Glu Ala Lys Thr Ala His Leu Ala Ser Asn Gly
     130                 135                 140

GAC TAC CCG TCG GGG CAC ACC GCC AAT GGT TGG CTG GAA GCG CAG ATC              480
Asp Tyr Pro Ser Gly His Thr Ala Asn Gly Trp Leu Glu Ala Gln Ile
145                 150                 155                 160

CTC GCC GAG GTG ATG CCC GAC AAG GCG ACT GCG ATC CTC GCG CGC GGC              528
Leu Ala Glu Val Met Pro Asp Lys Ala Thr Ala Ile Leu Ala Arg Gly
                 165                 170                 175

CGT GCC TAT GGC GAG AGC CGG GCG ATT TGC GGG TCG CAC AGC AAG AGC              576
Arg Ala Tyr Gly Glu Ser Arg Ala Ile Cys Gly Ser His Ser Lys Ser
             180                 185                 190

GCG GTC GAA GCC GGC TAC ATG GCC GGC GCC TCG GTG TTC GCG GTG CTG              624
Ala Val Glu Ala Gly Tyr Met Ala Gly Ala Ser Val Phe Ala Val Leu
         195                 200                 205

CAG ACC TCG CCC GCC TAC CAG CGG GAT CTC GCG GCG GCG CGG CAG GAA              672
Gln Thr Ser Pro Ala Tyr Gln Arg Asp Leu Ala Ala Ala Arg Gln Glu
     210                 215                 220

GCG GCG CGG CTG CGC ACT ACC GCG CCG CGC CCC GAT GCA CAA AGC TGT              720
Ala Ala Arg Leu Arg Thr Thr Ala Pro Arg Pro Asp Ala Gln Ser Cys
225                 230                 235                 240

GTC GCG GAA GCG GAG GCC CTT CGC GTC CGC CCC TGG                              756
Val Ala Glu Ala Glu Ala Leu Arg Val Arg Pro Trp
                 245                 250
```

(2) INFORMATION FOR SEQ ID NO:2:

(i) SEQUENCE CHARACTERISTICS:
        (A) LENGTH: 252 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Ile Arg Gly Gly Ile Phe Ala Ala Leu Ser Leu Leu Ile Ala Val
 1               5                  10                  15

Pro Gln Ala Ser Asp Thr Ala Pro Tyr Leu Ala Ala Gly Gln Tyr Pro
                20                  25                  30
```

Asp Gly Met Ala Ile Leu Pro Pro Pro Ala Leu Asp Ser Pro Gly
        35                  40                    45
Ala Ala Leu Asp Met Ala Val Phe Arg Ala Thr Arg Lys Leu Glu Gly
    50                  55                  60
Thr Pro Arg Trp Arg Ile Ala Thr Asp Asp Val Thr Asn Asp Pro Leu
65              70                      75                    80
Arg Arg Asn Ala Cys Ala Met Gly Met Val Leu Asp Val Lys Thr Ala
                85                  90                      95
Pro Ala Leu Ala Arg Leu Leu Asp Arg Ala Gly Thr Gly Pro Val Val
            100                 105                 110
Gly Arg Val Lys Ala Ala Tyr Gln Val Pro Arg Pro Tyr Leu Arg Glu
        115                 120                 125
Asp Gly Pro Ile Cys Glu Ala Lys Thr Ala His Leu Ala Ser Asn Gly
    130                 135                 140
Asp Tyr Pro Ser Gly His Thr Ala Asn Gly Trp Leu Glu Ala Gln Ile
145                 150                 155                 160
Leu Ala Glu Val Met Pro Asp Lys Ala Thr Ala Ile Leu Ala Arg Gly
                165                 170                 175
Arg Ala Tyr Gly Glu Ser Arg Ala Ile Cys Gly Ser His Ser Lys Ser
            180                 185                 190
Ala Val Glu Ala Gly Tyr Met Ala Gly Ala Ser Val Phe Ala Val Leu
        195                 200                 205
Gln Thr Ser Pro Ala Tyr Gln Arg Asp Leu Ala Ala Ala Arg Gln Glu
    210                 215                 220
Ala Ala Arg Leu Arg Thr Thr Ala Pro Arg Pro Asp Ala Gln Ser Cys
225                 230                 235                 240
Val Ala Glu Ala Glu Ala Leu Arg Val Arg Pro Trp
                245                 250

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: YES ( i x ) FEATURE:
        ( A ) NAME/KEY: CDS
        ( B ) LOCATION: 1..17

( i x ) FEATURE:
        ( A ) NAME/KEY: CDS
        ( B ) LOCATION: 1..17

( x i ) SEQUENCE DESCRIPTION: SEQ ID NO:3:

GCNATGGGNA TGGTNYT                                                                    17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES (iv) ANTI-SENSE: YES (ix) FEATURE:
    (A) NAME/KEY: CDS
    (B) LOCATION: 1..17

(xi) SEQUENCE DESCRIPTION: SEQ ID NO:4:

TCRCADATNG GNCCRTC    17